(12) United States Patent
Randolph et al.

(10) Patent No.: US 11,752,252 B2
(45) Date of Patent: Sep. 12, 2023

(54) ELECTRO-MECHANICAL PUMP FOR NEGATIVE-PRESSURE TREATMENT

(71) Applicant: KCI Licensing, Inc., San Antonio, TX (US)

(72) Inventors: Larry Tab Randolph, San Antonio, TX (US); Richard Marvin Kazala, Jr., San Antonio, TX (US)

(73) Assignee: KCI Licensing, Inc., San Antonio, TX (US)

( * ) Notice: Subject to any disclaimer, the term of this patent is extended or adjusted under 35 U.S.C. 154(b) by 179 days.

(21) Appl. No.: 16/541,433

(22) Filed: Aug. 15, 2019

(65) Prior Publication Data

US 2020/0069476 A1    Mar. 5, 2020

Related U.S. Application Data

(60) Provisional application No. 62/724,765, filed on Aug. 30, 2018.

(51) Int. Cl.
*A61M 1/00* (2006.01)
*A61F 13/00* (2006.01)
*F04B 43/00* (2006.01)

(52) U.S. Cl.
CPC ......... *A61M 1/82* (2021.05); *A61F 13/00068* (2013.01); *A61M 1/962* (2021.05); *F04B 43/0018* (2013.01); *A61M 1/916* (2021.05); *A61M 1/98* (2021.05)

(58) Field of Classification Search
CPC . A61F 13/00068; A61M 1/0066–0072; A61M 1/0088; A61M 16/08; A61M 16/0833; A61M 16/0816; A61M 16/0825; A61M 16/0072; A61M 16/0075; A61M 16/0078; A61M 16/0081; A61M 16/0084; F04B 43/0018
See application file for complete search history.

(56) References Cited

U.S. PATENT DOCUMENTS

| 1,355,846 A | 10/1920 | Rannells |
| 2,547,758 A | 4/1951 | Keeling |
| 2,632,443 A | 3/1953 | Lesher |
| 2,682,873 A | 7/1954 | Evans et al. |

(Continued)

FOREIGN PATENT DOCUMENTS

| AU | 550575 B2 | 3/1986 |
| AU | 745271 B2 | 3/2002 |

(Continued)

OTHER PUBLICATIONS

International Search Report and Written Opinion for Corresponding Application No. PCT/US2019/046619, dated Nov. 12, 2019.

(Continued)

*Primary Examiner* — Susan S Su
*Assistant Examiner* — Eric Rassavong

(57) ABSTRACT

An apparatus for negative-pressure treatment may include an enclosure having a variable volume, a port and an actuation surface, a first one-way valve configured to allow fluid ingress to the enclosure, a second one-way valve configured to allow fluid egress from the enclosure, and an actuator configured to apply a linear force to the actuation surface.

30 Claims, 3 Drawing Sheets

(56) References Cited

U.S. PATENT DOCUMENTS

| | | | |
|---|---|---|---|
| 2,910,763 A | 11/1959 | Lauterbach | |
| 2,969,057 A | 1/1961 | Simmons | |
| 3,066,672 A | 12/1962 | Crosby, Jr. et al. | |
| 3,200,816 A * | 8/1965 | Bartlett, Jr. | A62B 7/12 |
| | | | 128/205.12 |
| 3,367,332 A | 2/1968 | Groves | |
| 3,520,300 A | 7/1970 | Flower, Jr. | |
| 3,568,675 A | 3/1971 | Harvey | |
| 3,648,692 A | 3/1972 | Wheeler | |
| 3,682,180 A | 8/1972 | McFarlane | |
| 3,826,254 A | 7/1974 | Mellor | |
| 4,080,970 A | 3/1978 | Miller | |
| 4,096,853 A | 6/1978 | Weigand | |
| 4,139,004 A | 2/1979 | Gonzalez, Jr. | |
| 4,165,748 A | 8/1979 | Johnson | |
| 4,184,510 A | 1/1980 | Murry et al. | |
| 4,233,969 A | 11/1980 | Lock et al. | |
| 4,245,630 A | 1/1981 | Lloyd et al. | |
| 4,256,109 A | 3/1981 | Nichols | |
| 4,261,363 A | 4/1981 | Russo | |
| 4,275,721 A | 6/1981 | Olson | |
| 4,284,079 A | 8/1981 | Adair | |
| 4,297,995 A | 11/1981 | Golub | |
| 4,333,468 A | 6/1982 | Geist | |
| 4,373,519 A | 2/1983 | Errede et al. | |
| 4,382,441 A | 5/1983 | Svedman | |
| 4,392,853 A | 7/1983 | Muto | |
| 4,392,858 A | 7/1983 | George et al. | |
| 4,419,097 A | 12/1983 | Rowland | |
| 4,465,485 A | 8/1984 | Kashmer et al. | |
| 4,475,909 A | 10/1984 | Eisenberg | |
| 4,480,638 A | 11/1984 | Schmid | |
| 4,525,166 A | 6/1985 | Leclerc | |
| 4,525,374 A | 6/1985 | Vaillancourt | |
| 4,540,412 A | 9/1985 | Van Overloop | |
| 4,543,100 A | 9/1985 | Brodsky | |
| 4,548,202 A | 10/1985 | Duncan | |
| 4,551,139 A | 11/1985 | Plaas et al. | |
| 4,569,348 A | 2/1986 | Hasslinger | |
| 4,605,399 A | 8/1986 | Weston et al. | |
| 4,608,041 A | 8/1986 | Nielsen | |
| 4,640,688 A | 2/1987 | Hauser | |
| 4,655,754 A | 4/1987 | Richmond et al. | |
| 4,664,662 A | 5/1987 | Webster | |
| 4,710,165 A * | 12/1987 | McNeil | A61M 1/0023 |
| | | | 604/31 |
| 4,733,659 A | 3/1988 | Edenbaum et al. | |
| 4,743,232 A | 5/1988 | Kruger | |
| 4,758,220 A | 7/1988 | Sundblom et al. | |
| 4,787,888 A | 11/1988 | Fox | |
| 4,826,494 A | 5/1989 | Richmond et al. | |
| 4,838,883 A | 6/1989 | Matsuura | |
| 4,840,187 A | 6/1989 | Brazier | |
| 4,863,449 A | 9/1989 | Therriault et al. | |
| 4,872,450 A | 10/1989 | Austad | |
| 4,878,901 A | 11/1989 | Sachse | |
| 4,897,081 A | 1/1990 | Poirier et al. | |
| 4,906,233 A | 3/1990 | Moriuchi et al. | |
| 4,906,240 A | 3/1990 | Reed et al. | |
| 4,919,654 A | 4/1990 | Kalt | |
| 4,941,882 A | 7/1990 | Ward et al. | |
| 4,953,565 A | 9/1990 | Tachibana et al. | |
| 4,969,880 A | 11/1990 | Zamierowski | |
| 4,985,019 A | 1/1991 | Michelson | |
| 5,037,397 A | 8/1991 | Kalt et al. | |
| 5,086,170 A | 2/1992 | Luheshi et al. | |
| 5,092,858 A | 3/1992 | Benson et al. | |
| 5,100,396 A | 3/1992 | Zamierowski | |
| 5,134,994 A | 8/1992 | Say | |
| 5,149,331 A | 9/1992 | Ferdman et al. | |
| 5,167,613 A | 12/1992 | Karami et al. | |
| 5,176,663 A | 1/1993 | Svedman et al. | |
| 5,215,522 A | 6/1993 | Page et al. | |
| 5,232,453 A | 8/1993 | Plass et al. | |
| 5,261,893 A | 11/1993 | Zamierowski | |
| 5,278,100 A | 1/1994 | Doan et al. | |
| 5,279,550 A | 1/1994 | Habib et al. | |
| 5,298,015 A | 3/1994 | Komatsuzaki et al. | |
| 5,342,376 A | 8/1994 | Ruff | |
| 5,344,415 A | 9/1994 | DeBusk et al. | |
| 5,358,494 A | 10/1994 | Svedman | |
| 5,437,622 A | 8/1995 | Carion | |
| 5,437,651 A | 8/1995 | Todd et al. | |
| 5,527,293 A | 6/1996 | Zamierowski | |
| 5,549,584 A * | 8/1996 | Gross | A61M 1/0088 |
| | | | 604/313 |
| 5,556,375 A | 9/1996 | Ewall | |
| 5,607,388 A | 3/1997 | Ewall | |
| 5,636,643 A | 6/1997 | Argenta et al. | |
| 5,645,081 A | 7/1997 | Argenta et al. | |
| 6,071,267 A | 6/2000 | Zamierowski | |
| 6,135,116 A | 10/2000 | Vogel et al. | |
| 6,241,747 B1 | 6/2001 | Ruff | |
| 6,269,811 B1 * | 8/2001 | Duff | A61M 16/0069 |
| | | | 128/204.21 |
| 6,287,316 B1 | 9/2001 | Agarwal et al. | |
| 6,345,623 B1 | 2/2002 | Heaton et al. | |
| 6,488,643 B1 | 12/2002 | Tumey et al. | |
| 6,493,568 B1 | 12/2002 | Bell et al. | |
| 6,553,998 B2 | 4/2003 | Heaton et al. | |
| 6,814,079 B2 | 11/2004 | Heaton et al. | |
| 7,846,141 B2 | 12/2010 | Weston | |
| 8,062,273 B2 | 11/2011 | Weston | |
| 8,216,198 B2 | 7/2012 | Heagle et al. | |
| 8,251,979 B2 | 8/2012 | Malhi | |
| 8,257,327 B2 | 9/2012 | Blott et al. | |
| 8,398,614 B2 | 3/2013 | Blott et al. | |
| 8,449,509 B2 | 5/2013 | Weston | |
| 8,529,548 B2 | 9/2013 | Blott et al. | |
| 8,535,296 B2 | 9/2013 | Blott et al. | |
| 8,551,060 B2 | 10/2013 | Schuessler et al. | |
| 8,568,386 B2 | 10/2013 | Malhi | |
| 8,679,081 B2 | 3/2014 | Heagle et al. | |
| 8,834,451 B2 | 9/2014 | Blott et al. | |
| 8,926,592 B2 | 1/2015 | Blott et al. | |
| 9,017,302 B2 | 4/2015 | Vitaris et al. | |
| 9,198,801 B2 | 12/2015 | Weston | |
| 9,211,365 B2 | 12/2015 | Weston | |
| 9,289,542 B2 | 3/2016 | Blott et al. | |
| 2002/0077661 A1 | 6/2002 | Saadat | |
| 2002/0115951 A1 | 8/2002 | Norstrem et al. | |
| 2002/0120185 A1 | 8/2002 | Johnson | |
| 2002/0143286 A1 | 10/2002 | Tumey | |
| 2007/0179460 A1 * | 8/2007 | Adahan | F04B 43/067 |
| | | | 604/319 |
| 2011/0288510 A1 * | 11/2011 | Locke | A61M 1/0088 |
| | | | 604/319 |
| 2014/0163491 A1 | 6/2014 | Schuessler et al. | |
| 2014/0200535 A1 * | 7/2014 | Locke | A61M 1/0088 |
| | | | 604/321 |
| 2015/0080788 A1 | 3/2015 | Blott et al. | |
| 2016/0045375 A1 * | 2/2016 | Zurovcik | A61F 13/0253 |
| | | | 602/52 |
| 2016/0235932 A1 * | 8/2016 | Rankin | A61M 16/0075 |
| 2016/0367781 A1 * | 12/2016 | McCollum | A61M 16/0084 |
| 2017/0319758 A1 * | 11/2017 | Eddy | A61M 1/0003 |

FOREIGN PATENT DOCUMENTS

| | | |
|---|---|---|
| AU | 755496 B2 | 12/2002 |
| CA | 2005436 A1 | 6/1990 |
| DE | 26 40 413 A1 | 3/1978 |
| DE | 43 06 478 A1 | 9/1994 |
| DE | 29 504 378 U1 | 9/1995 |
| EP | 0100148 A1 | 2/1984 |
| EP | 0117632 A2 | 9/1984 |
| EP | 0161865 A2 | 11/1985 |
| EP | 0358302 A2 | 3/1990 |
| EP | 1018967 A1 | 7/2000 |
| EP | 1905465 A1 | 4/2008 |
| GB | 692578 A | 6/1953 |
| GB | 2195255 A | 4/1988 |
| GB | 2 197 789 A | 6/1988 |

(56) References Cited

FOREIGN PATENT DOCUMENTS

| | | | |
|---|---|---|---|
| GB | 2 220 357 A | 1/1990 | |
| GB | 2 235 877 A | 3/1991 | |
| GB | 2 329 127 A | 3/1999 | |
| GB | 2 333 965 A | 8/1999 | |
| JP | 4129536 B2 | 8/2008 | |
| SE | 0744184 A1 | * 11/1886 | |
| SG | 71559 | 4/2002 | |
| WO | 80/02182 A1 | 10/1980 | |
| WO | 87/04626 A1 | 8/1987 | |
| WO | 90/010424 A1 | 9/1990 | |
| WO | 93/009727 A1 | 5/1993 | |
| WO | 94/20041 A1 | 9/1994 | |
| WO | 96/05873 A1 | 2/1996 | |
| WO | 97/18007 A1 | 5/1997 | |
| WO | 99/13793 A1 | 3/1999 | |
| WO | 2016094742 A1 | 6/2016 | |

OTHER PUBLICATIONS

Louis C. Argenta, MD and Michael J. Morykwas, PHD; Vacuum-Assisted Closure: A New Method for Wound Control and Treatment: Clinical Experience; Annals of Plastic Surgery; vol. 38, No. 6, Jun. 1997; pp. 563-576.
Susan Mendez-Eatmen, RN; "When wounds Won't Heal" RN Jan. 1998, vol. 61 (1); Medical Economics Company, Inc., Montvale, NJ, USA; pp. 20-24.
James H. Blackburn II, MD et al.: Negative-Pressure Dressings as a Bolster for Skin Grafts; Annals of Plastic Surgery, vol. 40, No. 5, May 1998, pp. 453-457; Lippincott Williams & Wilkins, Inc., Philidelphia, PA, USA.
John Masters; "Reliable, Inexpensive and Simple Suction Dressings"; Letter to the Editor, British Journal of Plastic Surgery, 1998, vol. 51 (3), p. 267; Elsevier Science/The British Association of Plastic Surgeons, UK.
S.E. Greer, et al. "The Use of Subatmospheric Pressure Dressing Therapy to Close Lymphocutaneous Fistulas of the Groin" British Journal of Plastic Surgery (2000), 53, pp. 484-487.
George V. Letsou, MD., et al.; "Stimulation of Adenylate Cyclase Activity in Cultured Endothelial Cells Subjected to Cyclic Stretch"; Journal of Cardiovascular Surgery, 31, 1990, pp. 634-639.
Orringer, Jay, et al; "Management of Wounds in Patients with Complex Enterocutaneous Fistulas"; Surgery, Gynecology & Obstetrics, Jul. 1987, vol. 165, pp. 79-80.
International Search Report for PCT International Application PCT/GB95/01983; dated Nov. 23, 1995.
PCT International Search Report for PCT International Application PCT/GB98/02713; dated Jan. 8, 1999.
PCT Written Opinion; PCT International Application PCT/GB98/02713; dated Jun. 8, 1999.
PCT International Examination and Search Report, PCT International Application PCT/GB96/02802; dated Jan. 15, 1998 & dated Apr. 29, 1997.
PCT Written Opinion, PCT International Application PCT/GB96/02802; dated Sep. 3, 1997.
Dattilo, Philip P., Jr., et al; "Medical Textiles: Application of an Absorbable Barbed Bi-directional Surgical Suture"; Journal of Textile and Apparel, Technology and Management, vol. 2, Issue 2, Spring 2002, pp. 1-5.
Kostyuchenok, B.M., et al; "Vacuum Treatment in the Surgical Management of Purulent Wounds"; Vestnik Khirurgi, Sep. 1986, pp. 18-21 and 6 page English translation thereof.
Davydov, Yu. A., et al; "Vacuum Therapy in the Treatment of Purulent Lactation Mastitis"; Vestnik Khirurgi, May 14, 1986, pp. 66-70, and 9 page English translation thereof.
Yusupov. Yu.N., et al; "Active Wound Drainage", Vestnki Khirurgi, vol. 138, Issue 4, 1987, and 7 page English translation thereof.
Davydov, Yu.A., et al; "Bacteriological and Cytological Assessment of Vacuum Therapy for Purulent Wounds"; Vestnik Khirugi, Oct. 1988, pp. 48-52, and 8 page English translation thereof.
Davydov, Yu.A., et al; "Concepts for the Clinical-Biological Management of the Wound Process in the Treatment of Purulent Wounds by Means of Vacuum Therapy"; Vestnik Khirurgi, Jul. 7, 1980, pp. 132-136, and 8 page English translation thereof.
Chariker, Mark E., M.D., et al; "Effective Management of incisional and cutaneous fistulae with closed suction wound drainage"; Contemporary Surgery, vol. 34, Jun. 1989, pp. 59-63.
Egnell Minor, Instruction Book, First Edition, 300 7502, Feb. 1975, pp. 24.
Egnell Minor: Addition to the Users Manual Concerning Overflow Protection—Concerns all Egnell Pumps, Feb. 3, 1983, pp. 2.
Svedman, P.: "Irrigation Treatment of Leg Ulcers", The Lancet, Sep. 3, 1983, pp. 532-534.
Chinn, Steven D. et al.: "Closed Wound Suction Drainage", The Journal of Foot Surgery, vol. 24, No. 1, 1985, pp. 76-81.
Arnljots, Björn et al.: "Irrigation Treatment in Split-Thickness Skin Grafting of Intractable Leg Ulcers", Scand J. Plast Reconstr. Surg., No. 19, 1985, pp. 211-213.
Svedman, P.: "A Dressing Allowing Continuous Treatment of a Biosurface", IRCS Medical Science: Biomedical Technology, Clinical Medicine, Surgery and Transplantation, vol. 7, 1979, p. 221.
Svedman, P. et al: "A Dressing System Providing Fluid Supply and Suction Drainage Used for Continuous of Intermittent Irrigation", Annals of Plastic Surgery, vol. 17, No. 2, Aug. 1986, pp. 125-133.
N.A. Bagautdinov, "Variant of External Vacuum Aspiration in the Treatment of Purulent Diseases of Soft Tissues," Current Problems in Modern Clinical Surgery: Interdepartmental Collection, edited by V. Ye Volkov et al. (Chuvashia State University, Cheboksary, U.S.S.R. 1986); pp. 94-96 (certified translation).
K.F. Jeter, T.E. Tintle, and M. Chariker, "Managing Draining Wounds and Fistulae: New and Established Methods," Chronic Wound Care, edited by D. Krasner (Health Management Publications, Inc., King of Prussia, PA 1990), pp. 240-246.
G. Živadinovi?, V. ?uki?, Ž. Maksimovi?, ?. Radak, and P. Peška, "Vacuum Therapy in the Treatment of Peripheral Blood Vessels," Timok Medical Journal 11 (1986), pp. 161-164 (certified translation).
F.E. Johnson, "An Improved Technique for Skin Graft Placement Using a Suction Drain," Surgery, Gynecology, and Obstetrics 159 (1984), pp. 584-585.
A.A. Safronov, Dissertation Abstract, Vacuum Therapy of Trophic Ulcers of the Lower Leg with Simultaneous Autoplasty of the Skin (Central Scientific Research Institute of Traumatology and Orthopedics, Moscow, U.S.S.R. 1967) (certified translation).
M. Schein, R. Saadia, J.R. Jamieson, and G.A.G. Decker, "The 'Sandwich Technique' in the Management of the Open Abdomen," British Journal of Surgery 73 (1986), pp. 369-370.
D.E. Tribble, An Improved Sump Drain-Irrigation Device of Simple Construction, Archives of Surgery 105 (1972) pp. 511-513.
M.J. Morykwas, L.C. Argenta, E.I. Shelton-Brown, and W. McGuirt, "Vacuum-Assisted Closure: A New Method for Wound Control and Treatment: Animal Studies and Basic Foundation," Annals of Plastic Surgery 38 (1997), pp. 553-562 (Morykwas I).
C.E. Tennants, "The Use of Hypermia in the Postoperative Treatment of Lesions of the Extremities and Thorax," Journal of the American Medical Association 64 (1915), pp. 1548-1549.
Selections from W. Meyer and V. Schmieden, Bier's Hyperemic Treatment in Surgery, Medicine, and the Specialties: A Manual of Its Practical Application, (W.B. Saunders Co., Philadelphia, PA 1909), pp. 17-25, 44-64, 90-96, 167-170, and 210-211.
V.A. Solovev et al., Guidelines, The Method of Treatment of Immature External Fistulas in the Upper Gastrointestinal Tract, editor-in-chief Prov. V.I. Parahonyak (S.M. Kirov Gorky State Medical Institute, Gorky, U.S.S.R. 1987) ("Solovev Guidelines").
V.A. Kuznetsov & N.a. Bagautdinov, "Vacuum and Vacuum-Sorption Treatment of Open Septic Wounds," in II All-Union Conference on Wounds and Wound Infections: Presentation Abstracts, edited by B.M. Kostyuchenok et al. (Moscow, U.S.S.R. Oct. 28-29, 1986) pp. 91-92 ("Bagautdinov II").
V.A. Solovev, Dissertation Abstract, Treatment and Prevention of Suture Failures after Gastric Resection (S.M. Kirov Gorky State Medical Institute, Gorky, U.S.S.R. 1988) ("Solovev Abstract").

(56) References Cited

OTHER PUBLICATIONS

V.A.C.® Therapy Clinical Guidelines: A Reference Source for Clinicians; Jul. 2007.

* cited by examiner

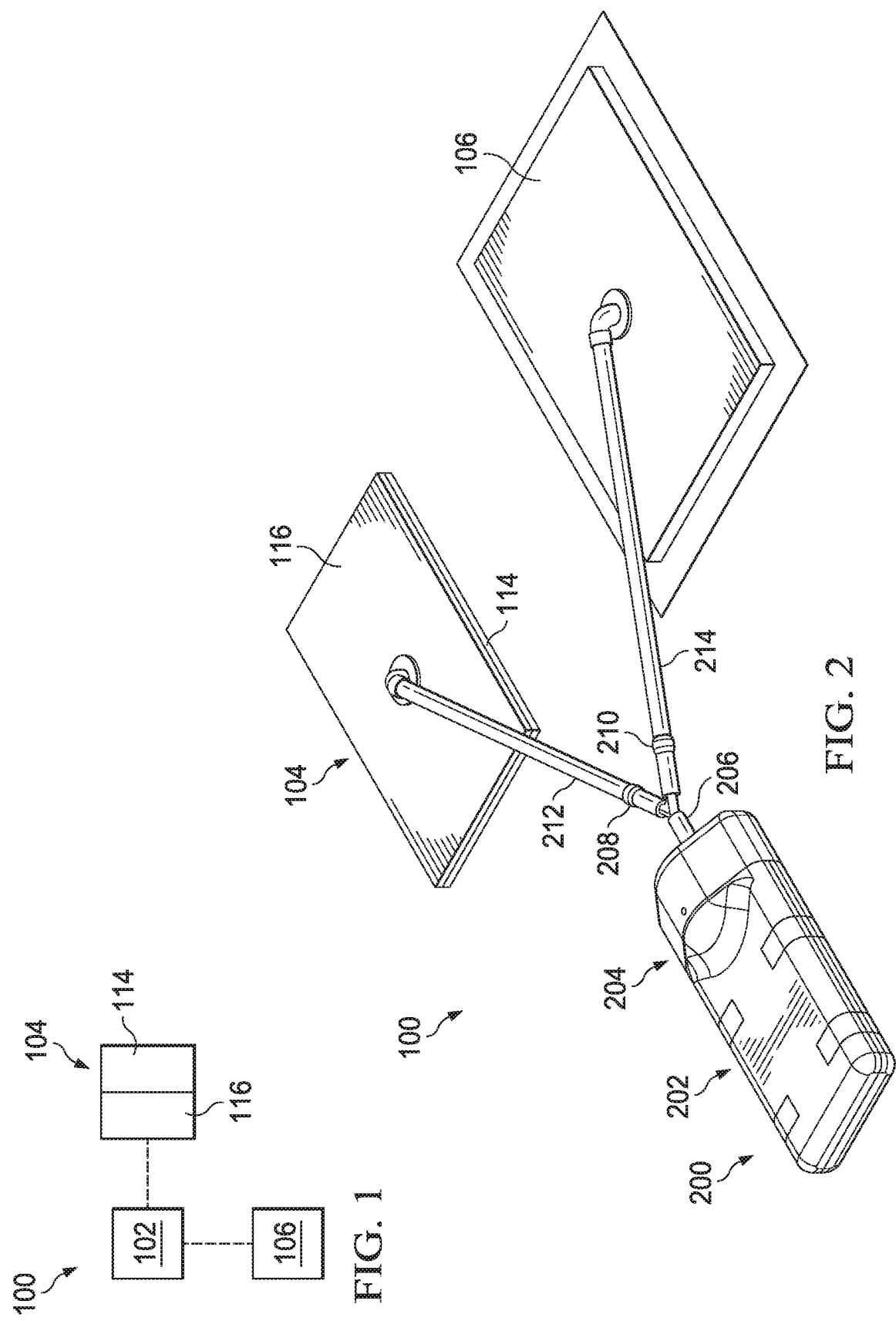

ELECTRO-MECHANICAL PUMP FOR NEGATIVE-PRESSURE TREATMENT

RELATED APPLICATIONS

The present application claims the benefit, under 35 USC § 119(e), of the filing of U.S. Provisional Patent Application Ser. No. 62/724,765, entitled "Electro-Mechanical Pump for Negative-Pressure Treatment," filed Aug. 30, 2018, which is incorporated herein by reference for all purposes.

TECHNICAL FIELD

The invention set forth in the appended claims relates generally to tissue treatment systems and more particularly, but without limitation, to a pump for applying negative-pressure to dressings and methods of using the pump for negative-pressure treatment.

BACKGROUND

Clinical studies and practice have shown that reducing pressure in proximity to a tissue site can augment and accelerate growth of new tissue at the tissue site. The applications of this phenomenon are numerous, but it has proven particularly advantageous for treating wounds. Regardless of the etiology of a wound, whether trauma, surgery, or another cause, proper care of the wound is important to the outcome. Treatment of wounds or other tissue with reduced pressure may be commonly referred to as "negative-pressure therapy," but is also known by other names, including "negative-pressure wound therapy," "reduced-pressure therapy," "vacuum therapy," "vacuum-assisted closure," and "topical negative-pressure," for example. Negative-pressure therapy may provide a number of benefits, including migration of epithelial and subcutaneous tissues, improved blood flow, and micro-deformation of tissue at a wound site. Together, these benefits can increase development of granulation tissue and reduce healing times.

While the clinical benefits of negative-pressure therapy are widely known, improvements to therapy systems, components, and processes may benefit healthcare providers and patients.

BRIEF SUMMARY

New and useful systems, apparatuses, and methods for applying negative-pressure to a dressing are set forth in the appended claims. Illustrative embodiments are also provided to enable a person skilled in the art to make and use the claimed subject matter.

For example, in some embodiments, an apparatus for applying negative pressure may comprise an electro-mechanical pump, such as a bellows pump, which may be configured to achieve high or low flow rates. The apparatus may additionally include a tubing set that is separable from the pump in some examples. At least some portions of the pump may be fluidly isolated from the tubing set. At least some portions of the pump may be reusable, and some portions (such as the tubing set) may be disposable.

In some examples, the pump may include a geared motor configured to drive a linear actuator that compresses a bellows. Additionally or alternatively, the pump may be manually operated in some configurations. When the bellows is compressed, contents of the bellows, which may be mostly air, can be expelled through a first one-way valve, such as a duckbill valve, to a vented bag. If the linear actuator is retracted, the bellows can decompress without the linear actuator's assistance. During decompression of the bellows, contents of a closed dressing, which may be mostly air, may be drawn out of the dressing and into the bellows through a second one-way valve, such as a duckbill valve. Compression and decompression of the bellows can continue until the bellows no longer decompresses. Once the bellows no longer decompresses, the closed dressing is at a preset vacuum level. The vacuum level of the bellows may be altered by varying the material and/or the wall thickness of the bellows, for example.

More generally, an apparatus for negative-pressure treatment may include an enclosure having a variable volume, a port and an actuation surface, a first one-way valve configured to allow fluid ingress to the enclosure, a second one-way valve configured to allow fluid egress from the enclosure, and an actuator configured to apply a linear force to the actuation surface. In some examples, the actuator may be detachably coupled to or otherwise separable from the actuation surface.

Alternatively, other example embodiments may include an apparatus for negative-pressure treatment. The apparatus may include a dressing, an enclosure having a variable volume, a container fluidly coupled to the dressing through the enclosure, a first one-way valve configured to allow fluid ingress to the enclosure from the dressing, and a second one-way valve configured to allow fluid egress from the enclosure to the container.

Objectives, advantages, and a preferred mode of making and using the claimed subject matter may be understood best by reference to the accompanying drawings in conjunction with the following detailed description of illustrative embodiments. In some embodiments, the bellows and the two one-way valves may be part of a disposable tubing portion that can be attached to a dressing and a vented bag. At least some parts of the pump may be reusable. The pump may be designed to reduce electronic costs, may be designed for different flow rates, may be manually operated, may eliminate a need for a rigid canister, may eliminate fluid ingress into the device, and can work on a constant force curve irrelevant of the vacuum load on the system so as to reduce power draw.

BRIEF DESCRIPTION OF THE DRAWINGS

FIG. 1 is a functional block diagram of an example embodiment of a therapy system that can provide negative-pressure therapy in accordance with this specification;

FIG. 2 is a schematic view of an example of the therapy system of FIG. 1, illustrating additional details that may be associated with some embodiments;

DESCRIPTION OF EXAMPLE EMBODIMENTS

Figure 3:
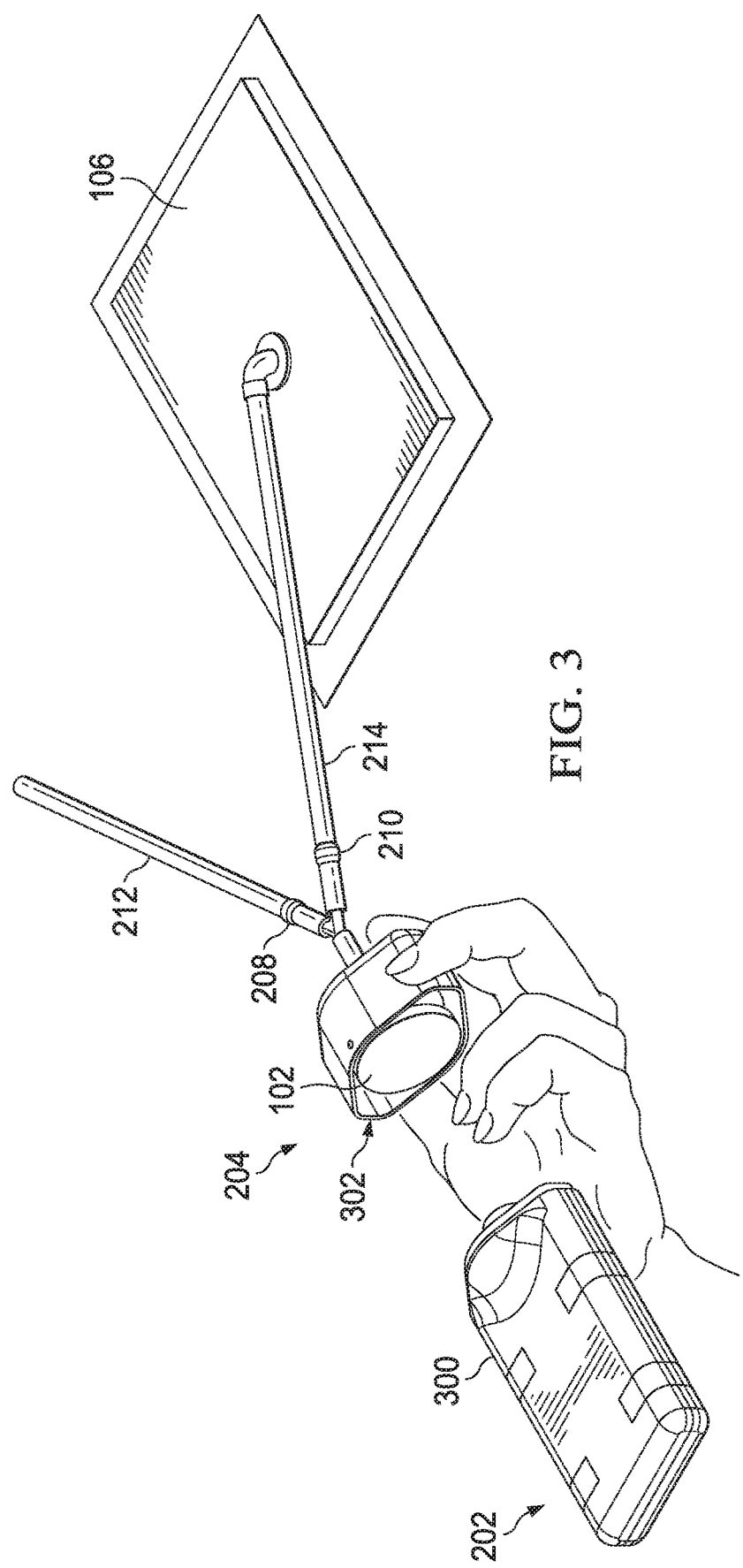
FIG. 3 is another schematic view the example therapy system of FIG. 2 illustrating additional details that may be associated with some embodiments.

The following description of example embodiments provides information that enables a person skilled in the art to make and use the subject matter set forth in the appended claims, but may omit certain details already well-known in the art. The following detailed description is, therefore, to be taken as illustrative and not limiting.

The example embodiments may also be described herein with reference to spatial relationships between various elements or to the spatial orientation of various elements depicted in the attached drawings. In general, such relationships or orientation assume a frame of reference consistent with or relative to a patient in a position to receive treatment. However, as should be recognized by those skilled in the art, this frame of reference is merely a descriptive expedient rather than a strict prescription.

FIG. 1 is a simplified functional block diagram of an example embodiment of a therapy system 100 that can provide negative-pressure therapy to a tissue site in accordance with this specification.

The term "tissue site" in this context broadly refers to a wound, defect, or other treatment target located on or within tissue, including but not limited to, bone tissue, adipose tissue, muscle tissue, neural tissue, dermal tissue, vascular tissue, connective tissue, cartilage, tendons, or ligaments. A wound may include chronic, acute, traumatic, subacute, and dehisced wounds, partial-thickness burns, ulcers (such as diabetic, pressure, or venous insufficiency ulcers), flaps, and grafts, for example. The term "tissue site" may also refer to areas of any tissue that are not necessarily wounded or defective, but are instead areas in which it may be desirable to add or promote the growth of additional tissue. For example, negative pressure may be applied to a tissue site to grow additional tissue that may be harvested and transplanted.

"Negative pressure" generally refers to a pressure less than a local ambient pressure, such as the ambient pressure in a local environment external to a sealed therapeutic environment. In many cases, the local ambient pressure may also be the atmospheric pressure at which a tissue site is located. Alternatively, the pressure may be less than a hydrostatic pressure associated with tissue at the tissue site. Unless otherwise indicated, values of pressure stated herein are gauge pressures. References to increases in negative pressure typically refer to a decrease in absolute pressure, while decreases in negative pressure typically refer to an increase in absolute pressure. While the amount and nature of negative pressure applied to a tissue site may vary according to therapeutic requirements, the pressure is generally a low vacuum, also commonly referred to as a rough vacuum, between −5 mm Hg (−667 Pa) and −500 mm Hg (−66.7 kPa). Common therapeutic ranges are between −75 mm Hg (−9.9 kPa) and −300 mm Hg (−39.9 kPa).

The therapy system 100 may include a source or supply of negative pressure, such as a negative-pressure source 102, and one or more distribution components. A distribution component is preferably detachable and may be disposable, reusable, or recyclable. A dressing, such as a dressing 104, and a fluid container, such as a container 106, are examples of distribution components that may be associated with some examples of the therapy system 100. One or distribution components, such as the dressing 104, may provide a fluid path between the negative-pressure source 102 and a tissue site. As illustrated in the example of FIG. 1, the dressing 104 may comprise or consist essentially of a tissue interface 114, a cover 116, or both in some embodiments.

A fluid conductor is another illustrative example of a distribution component. A "fluid conductor," in this context, broadly includes a tube, pipe, hose, conduit, or other structure with one or more lumina or open pathways adapted to convey a fluid between two ends. Typically, a tube is an elongated, cylindrical structure with some flexibility, but the geometry and rigidity may vary. Moreover, some fluid conductors may be molded into or otherwise integrally combined with other components. Distribution components may also include or comprise interfaces or fluid ports to facilitate coupling and de-coupling other components. In some embodiments, for example, a dressing interface may facilitate coupling a fluid conductor to the dressing 104. For example, such a dressing interface may be a SENSA-T.R.A.C.™ Pad available from Kinetic Concepts, Inc. of San Antonio, Tex.

In general, components of the therapy system 100 may be coupled directly or indirectly. For example, the negative-pressure source 102 may be directly coupled to the container 106, and the container 106 may be indirectly coupled to the dressing 104 through the negative-pressure source 102. Coupling may include fluid, mechanical, thermal, electrical, or chemical coupling (such as a chemical bond), or some combination of coupling in some contexts. In some embodiments, components may also be coupled by virtue of physical proximity, being integral to a single structure, or being formed from the same piece of material. For example, the negative-pressure source 102 may be fluidly and mechanically coupled to the dressing 104 in some embodiments.

The container 106 is representative of a container, canister, pouch, bag, or other storage component, which can be used to manage exudates and other fluids withdrawn from a tissue site. In many environments, a rigid container may be preferred or required for collecting, storing, and disposing of fluids. In other environments, fluids may be properly disposed of without rigid container storage, and a re-usable container could reduce waste and costs associated with negative-pressure therapy.

The tissue interface 114 can be generally adapted to contact a tissue site. The tissue interface 114 may be partially or fully in contact with the tissue site. If the tissue site is a wound, for example, the tissue interface 114 may partially or completely fill the wound, or may be placed over the wound. The tissue interface 114 may take many forms, and may have many sizes, shapes, or thicknesses depending on a variety of factors, such as the type of treatment being implemented or the nature and size of a tissue site. For example, the size and shape of the tissue interface 114 may be adapted to the contours of deep and irregular shaped tissue sites. Moreover, any or all of the surfaces of the tissue interface 114 may have projections or an uneven, course, or jagged profile that can induce strains and stresses on a tissue site, which can promote granulation at the tissue site.

In some embodiments, the tissue interface 114 may be a manifold. A "manifold" in this context generally includes any substance or structure providing a plurality of pathways adapted to collect or distribute fluid across a tissue site under pressure. For example, a manifold may be adapted to receive negative pressure from a source and distribute negative pressure through multiple apertures across a tissue site, which may have the effect of collecting fluid from across a tissue site and drawing the fluid toward the source.

In some illustrative embodiments, the pathways of a manifold may be interconnected to improve distribution or collection of fluids across a tissue site. In some illustrative embodiments, a manifold may be a porous foam material having interconnected cells or pores. For example, cellular foam, open-cell foam, reticulated foam, porous tissue collections, and other porous material such as gauze or felted mat generally include pores, edges, and/or walls adapted to form interconnected fluid channels. Liquids, gels, and other foams may also include or be cured to include apertures and fluid pathways. In some embodiments, a manifold may additionally or alternatively comprise projections that form interconnected fluid pathways. For example, a manifold may be molded to provide surface projections that define interconnected fluid pathways.

The average pore size of a foam may vary according to needs of a prescribed therapy. For example, in some embodiments, the tissue interface 114 may be a foam having pore sizes in a range of 400-600 microns. The tensile strength of the tissue interface 114 may also vary according to needs of a prescribed therapy. For example, the tensile strength of a foam may be increased for instillation of topical treatment solutions. In one non-limiting example, the tissue interface 114 may be an open-cell, reticulated polyurethane foam such as GRANUFOAM™ dressing or V.A.C. VERAFLO™ dressing, both available from KCI of San Antonio, Tex.

The tissue interface 114 may be either hydrophobic or hydrophilic. In an example in which the tissue interface 114 may be hydrophilic, the tissue interface 114 may also wick fluid away from a tissue site, while continuing to distribute negative pressure to the tissue site. The wicking properties of the tissue interface 114 may draw fluid away from a tissue site by capillary flow or other wicking mechanisms. An example of a hydrophilic foam is a polyvinyl alcohol, open-cell foam such as V.A.C. WHITEFOAM™ dressing available from KCI of San Antonio, Tex. Other hydrophilic foams may include those made from polyether. Other foams that may exhibit hydrophilic characteristics include hydrophobic foams that have been treated or coated to provide hydrophilicity.

The tissue interface 114 may further promote granulation at a tissue site when pressure within the sealed therapeutic environment is reduced. For example, any or all of the surfaces of the tissue interface 114 may have an uneven, coarse, or jagged profile that can induce microstrains and stresses at a tissue site if negative pressure is applied through the tissue interface 114.

In some embodiments, the tissue interface 114 may be constructed from bioresorbable materials. Suitable bioresorbable materials may include, without limitation, a polymeric blend of polylactic acid (PLA) and polyglycolic acid (PGA). The polymeric blend may also include without limitation polycarbonates, polyfumarates, and capralactones. The tissue interface 114 may further serve as a scaffold for new cell-growth, or a scaffold material may be used in conjunction with the tissue interface 114 to promote cell-growth. A scaffold is generally a substance or structure used to enhance or promote the growth of cells or formation of tissue, such as a three-dimensional porous structure that provides a template for cell growth. Illustrative examples of scaffold materials include calcium phosphate, collagen, PLA/PGA, coral hydroxy apatites, carbonates, or processed allograft materials.

In some embodiments, the cover 116 may provide a bacterial barrier and protection from physical trauma. The cover 116 may also be constructed from a material that can reduce evaporative losses and provide a fluid seal between two components or two environments, such as between a therapeutic environment and a local external environment. The cover 116 may comprise or consist of, for example, an elastomeric film or membrane that can provide a seal adequate to maintain a negative pressure at a tissue site for a given negative-pressure source. The cover 116 may have a high moisture-vapor transmission rate (MVTR) in some applications. For example, the MVTR may be at least 250 grams per square meter per twenty-four hours in some embodiments, measured using an upright cup technique according to ASTM E96/E96M Upright Cup Method at 38° C. and 10% relative humidity (RH). In some embodiments, an MVTR up to 5,000 grams per square meter per twenty-four hours may provide effective breathability and mechanical properties.

In some example embodiments, the cover 116 may be a polymer drape, such as a polyurethane film, that is permeable to water vapor but impermeable to liquid. Such drapes typically have a thickness in the range of 25-50 microns. For permeable materials, the permeability generally should be low enough that a desired negative pressure may be maintained. The cover 116 may comprise, for example, one or more of the following materials: polyurethane (PU), such as hydrophilic polyurethane; cellulosics; hydrophilic polyamides; polyvinyl alcohol; polyvinyl pyrrolidone; hydrophilic acrylics; silicones, such as hydrophilic silicone elastomers; natural rubbers; polyisoprene; styrene butadiene rubber; chloroprene rubber; polybutadiene; nitrile rubber; butyl rubber; ethylene propylene rubber; ethylene propylene diene monomer; chlorosulfonated polyethylene; polysulfide rubber; ethylene vinyl acetate (EVA); co-polyester; and polyether block polymide copolymers. Such materials are commercially available as, for example, Tegaderm® drape, commercially available from 3M Company, Minneapolis Minn.; polyurethane (PU) drape, commercially available from Avery Dennison Corporation, Pasadena, Calif.; polyether block polyamide copolymer (PEBAX), for example, from Arkema S.A., Colombes, France; and Inspire 2301 and Inpsire 2327 polyurethane films, commercially available from Expopack Advanced Coatings, Wrexham, United Kingdom. In some embodiments, the cover 116 may comprise INSPIRE 2301 having an MVTR (upright cup technique) of 2600 g/m²/24 hours and a thickness of about 30 microns.

An attachment device may be used to attach the cover 116 to an attachment surface, such as undamaged epidermis, a gasket, or another cover. The attachment device may take many forms. For example, an attachment device may be a medically-acceptable, pressure-sensitive adhesive configured to bond the cover 116 to epidermis around a tissue site. In some embodiments, for example, some or all of the cover 116 may be coated with an adhesive, such as an acrylic adhesive, which may have a coating weight of about 25-65 grams per square meter (g.s.m.). Thicker adhesives, or combinations of adhesives, may be applied in some embodiments to improve the seal and reduce leaks. Other example embodiments of an attachment device may include a double-sided tape, paste, hydrocolloid, hydrogel, silicone gel, or organogel.

The fluid mechanics of using a negative-pressure source to reduce pressure in another component or location, such as within a sealed therapeutic environment, can be mathematically complex. However, the basic principles of fluid mechanics applicable to negative-pressure therapy are generally well-known to those skilled in the art, and the process of reducing pressure may be described illustratively herein as "delivering," "distributing," or "generating" negative pressure, for example.

In general, exudates and other fluids flow toward lower pressure along a fluid path. Thus, the term "downstream" typically implies something in a fluid path relatively closer to a source of negative pressure or further away from a source of positive pressure. Conversely, the term "upstream" implies something relatively further away from a source of negative pressure or closer to a source of positive pressure. Similarly, it may be convenient to describe certain features in terms of fluid "inlet" or "outlet" in such a frame of reference. This orientation is generally presumed for purposes of describing various features and components herein. However, the fluid path may also be reversed in some applications (such as by substituting a positive-pressure source for a negative-pressure source) and this descriptive convention should not be construed as a limiting convention.

In operation, the tissue interface 114 may be placed within, over, on, or otherwise proximate to a tissue site. The cover 116 may be placed over the tissue interface 114 and sealed to an attachment surface near the tissue site. For example, the cover 116 may be sealed to undamaged epidermis peripheral to a tissue site. Thus, the dressing 104 can provide a sealed therapeutic environment proximate to a tissue site, substantially isolated from the external environment, and the negative-pressure source 102 can reduce the pressure in the sealed therapeutic environment. Negative pressure applied across the tissue site through the tissue interface 114 in the sealed therapeutic environment can induce macrostrain and micro-strain in the tissue site, as well as remove exudates and other fluids from the tissue site, which can be collected in container 106.

FIG. 2 is a schematic diagram illustrating additional details that may be associated with some example embodiments of the therapy system 100. As illustrated in the example of FIG. 2, therapy system 100 may include a therapy unit 200, which may include an actuator unit 202 and a pump unit 204 in some embodiments. In some embodiments, the actuator unit 202, the pump unit 204, or both may be generally rectangular in shape, and may be sized and configured to be handheld. For example, one or both of the actuator unit 202 and the pump unit 204 may have various ergonomic features, such as curved edges and corners.

The pump unit 204 may comprise a port 206, which can be fluidly coupled to the dressing 104 through a first valve 208. The port 206 may also be fluidly coupled to the container 106 through a second valve 210. In some embodiments, the first valve 208 and the second valve 210 may be one-way valves. For example, one or more of the first valve 208 and the second valve 210 may be a duck-bill valve in some embodiments.

In the example of FIG. 2, a first fluid conductor, such as tubing 212, may fluidly couple the dressing 104 to the first valve 208. The container 106 may be in fluid communication with the second valve 210 via a second fluid conductor, such as tubing 214. In some embodiments, the container 106 may be a vented bag, as illustrated in the example of FIG. 2.

FIG. 3 is an exploded view of the therapy system 100 of FIG. 2 without the dressing 104. As illustrated in the example of FIG. 3, some embodiments of the actuator unit 202 may include an actuator housing 300, and the pump unit 204 may include a pump housing 302. In the example of FIG. 3, the negative-pressure source 102 may be disposed within the pump housing 302.

Figure 4:
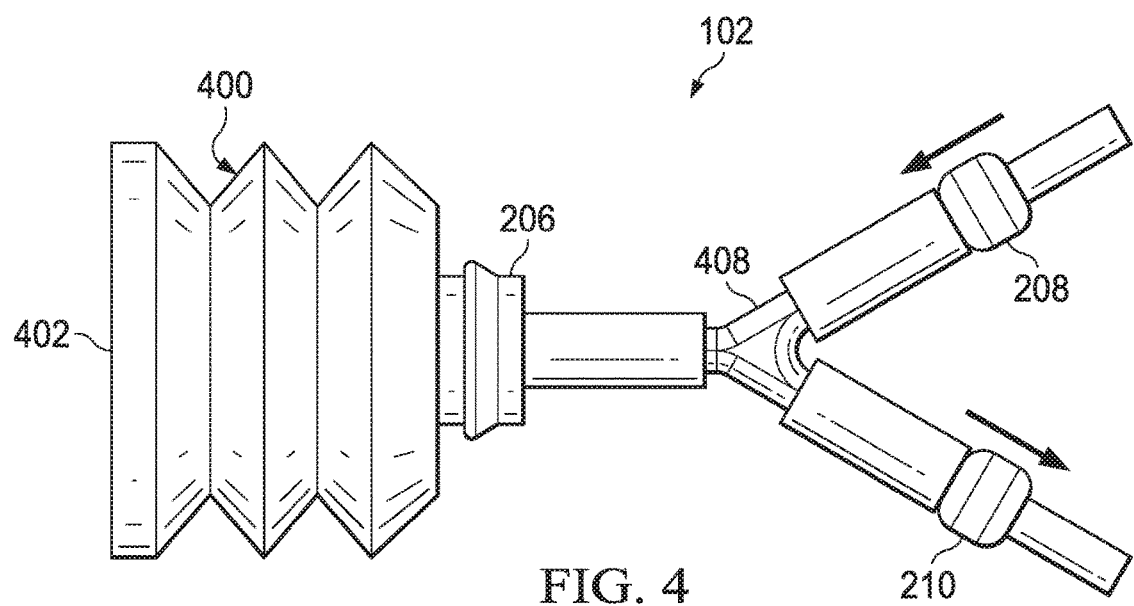
FIG. 4 is schematic view of a first portion of the therapy system of FIG. 3, illustrating additional details that may be associated with some embodiments.

FIG. 4 is schematic view of the negative-pressure source 102 of FIG. 3, illustrating additional details that may be associated with some embodiments. In the example of FIG. 4, the negative-pressure source 102 comprises or consists essentially of a pump with a chamber or other enclosure having a variable volume. For example the negative-pressure source 102 may comprise a chamber having flexible sides, such as a bellows 400 with concertinaed sides. The bellows 400 may have an actuation surface 402 at a first end. As illustrated in the example of FIG. 4, the actuation surface 402 may be generally flat in some embodiments. The port 206 may be fluidly coupled to a second end of the bellows 400. A Y-connector 404 may fluidly couple the port 206 to the first valve 208 and to the second valve 210.

The bellows 400 may be configured to generate a range of therapeutic negative pressure by varying the material or thickness of the flexible sides. In some examples, expansion of the bellows 400 can be configured to generate a negative pressure in a range of about 115 mmHg to about 135 mmHg. Moreover, a geometry of the bellows 400 may be chosen to maximize and/or increase a volume of the bellows 400 and/or a required or desired flow rate. For example, the flow rate is proportional to the volume of the bellows 400, which is proportional to the cross-sectional area and the height of the bellows 400. Consequently, the dimensions of the bellows 400 can be configured to generate a flow rate (for a given actuation rate) in a desired range.

Figure 5:
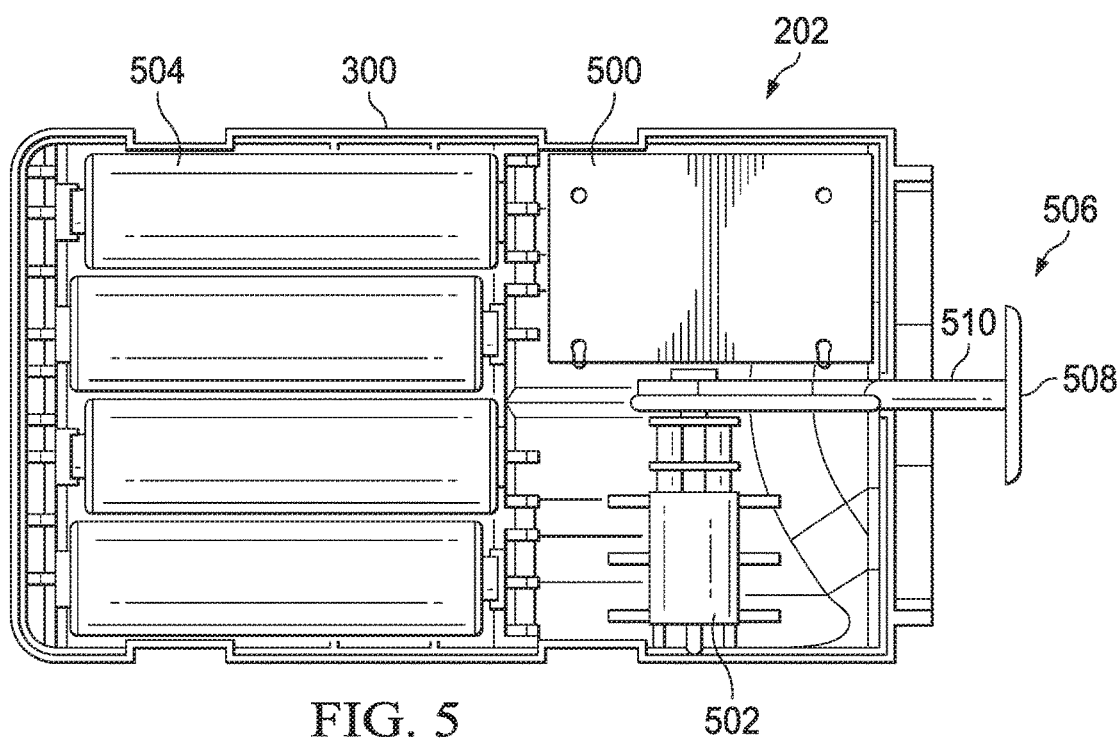
FIG. 5 is a schematic view of a second portion of the therapy system of FIG. 3, illustrating additional details that may be associated with some embodiments.

FIG. 5 is a schematic interior view of the actuator unit of FIG. 2, illustrating additional details that may be associated with some examples. In the example of FIG. 5, the actuator unit 202 may include a circuit board 500, an actuator drive 502, a power supply 504, and an actuator 506 contained within the actuator housing 300.

In some embodiments, the circuit board 500 may be configured to receive power from the power supply 504, which may comprise one or more small dry cell batteries. For example, standard AA batteries having an output voltage of 1.5 volts may be suitable for some configurations. The circuit board 500 may also be configured to periodically operate the actuator drive 502 and to receive a voltage feedback signal from the actuator drive 502. The circuit board 500 may be a logic circuit board with an on/off switch in some examples.

In some examples, the actuator drive 502 may include an electric motor, such as a gearmotor. A gearmotor having a ratio of about 250:1 and an output speed of about 60 revolutions per minute may be particularly suitable for some embodiments. In some embodiments, the actuator drive 502 may comprise or consist essentially of a solenoid valve.

In some embodiments, the actuator 506 is coupled to the actuator drive 502, as illustrated in the example of FIG. 5. For example, the actuator 506 may comprise an actuator surface 508 coupled to a shaft 510, which may be coupled to the actuator drive 502.

The actuator 506 is configured to engage the actuation surface 402 if assembled as in the example of FIG. 2. More particularly, the actuator surface 508 may be configured to engage the actuation surface 402 in some embodiments. During operation, the circuit board 500 may be configured to periodically operate the actuator drive 502, which in turn linearly drives the actuator 506 to produce alternating extension and retraction strokes.

In an extension stroke, the actuator 506 can engage to the actuation surface 402 to apply a compression force. A compression force on the actuation surface 402 can collapse the flexible sides of the bellows 400, which can decrease the volume of the bellows 400 and increase the pressure on any fluid in the bellows 400. Increased pressure on any fluid contents of the bellows 400 can expelled the fluid contents through the port 206. The first valve 208 can prevent fluid flow through the tubing 212 to the dressing 104, and the increased pressure of the fluid in the bellows 400 can open the second valve 210 to allow fluid flow to the container 106. In some embodiments, the contents of the bellows 400 may mainly include air.

In a retraction stroke, the actuator 506 is retracted from the actuation surface 402, removing the compression force from the bellows 400. Removing the compression force from the bellows 400 can allow the flexible sides of the bellows 400 to expand the volume of the bellows 400. Notably, no external force may be required to expand the volume. The increased volume of the bellows 400 can decrease the pressure in the bellows 400, which can cause any fluid contents of the dressing 104 to be drawn through the first valve 208 into the bellows 400.

The systems, apparatuses, and methods described herein may provide significant advantages. For example, in some embodiments, the actuator unit 202 is fluidly isolated from the pump unit 204 and may be decoupled from the pump unit 204. Since the actuator unit 202 can be fluidly isolated from the pump unit 204, decoupling the actuator unit 202 can allow the actuator unit 202 to be re-used. The pump unit 204 may be disposable in some embodiments. Additionally or alternatively, decoupling the pump unit 204 from the actuator unit 202 can allow the negative-pressure source 102 to be manually operated in some embodiments. Moreover, a pump with a compressible chamber, such as the bellows 400, can be designed to stay compressed at a set vacuum level, which can eliminate the need for pressure transducers or other sensors. Further, because the contents of the dressing 104 can be expelled on compression, the container 106 may be an inexpensive vented bag in some embodiments. Additionally, the compression force may remain constant irrelevant of the vacuum level on the dressing 104 because fluid can be expelled to atmospheric pressure in some embodiments, which can also reduce power draw.

While shown in a few illustrative embodiments, a person having ordinary skill in the art will recognize that the systems, apparatuses, and methods described herein are susceptible to various changes and modifications that fall within the scope of the appended claims. Moreover, descriptions of various alternatives using terms such as "or" do not require mutual exclusivity unless clearly required by the context, and the indefinite articles "a" or "an" do not limit the subject to a single instance unless clearly required by the context. Components may be also be combined or eliminated in various configurations for purposes of sale, manufacture, assembly, or use. For example, in some configurations the dressing 102, the container 112, or both may be eliminated or separated from other components for manufacture or sale. In other example configurations, the controller 108 may also be manufactured, configured, assembled, or sold independently of other components.

The appended claims set forth novel and inventive aspects of the subject matter described above, but the claims may also encompass additional subject matter not specifically recited in detail. For example, certain features, elements, or aspects may be omitted from the claims if not necessary to distinguish the novel and inventive features from what is already known to a person having ordinary skill in the art. Features, elements, and aspects described in the context of some embodiments may also be omitted, combined, or replaced by alternative features serving the same, equivalent, or similar purpose without departing from the scope of the invention defined by the appended claims.

What is claimed is:

1. An apparatus for negative-pressure treatment, the apparatus comprising:
   an enclosure having a variable volume, a port and an actuation surface;
   a first one-way valve coupled to the port and configured to allow fluid ingress to the enclosure through the port;
   a second one-way valve coupled to the port and configured to allow fluid egress from the enclosure through the port; and
   an actuator configured to apply a linear force to the actuation surface, the actuator comprising a linearly driven shaft and contact surface;
   wherein the variable volume is configured to expand to generate a negative pressure in a range of about 115 mmHg to about 135 mmHg in response to the linear force being removed from the actuation surface.

2. The apparatus of claim 1, further comprising a vented container fluidly coupled to the second one-way valve.

3. The apparatus of claim 1, further comprising an actuator driver coupled to the actuator.

4. The apparatus of claim 1, further comprising:
   an actuator driver coupled to the actuator; and
   a circuit board configured to periodically operate the actuator driver to apply the linear force to the actuation surface through the actuator.

5. The apparatus of claim 3, wherein the actuator driver comprises an electric motor.

6. The apparatus of claim 5, wherein the electric motor is a gear motor.

7. The apparatus of claim 5, further comprising a battery electrically coupled to the electric motor.

8. The apparatus of claim 7, wherein the circuit board is further configured to receive a voltage feedback signal from the electric motor.

9. The apparatus of claim 3, wherein the actuator driver comprises a solenoid valve.

10. The apparatus of claim 1, further comprising a dressing fluidly coupled to the first one-way valve.

11. The apparatus of claim 1, wherein the actuator is detachably coupled to the actuation surface.

12. The apparatus of claim 1, wherein the actuator is fluidly isolated from the variable volume.

13. The apparatus of claim 4, wherein the circuit board is fluidly isolated from the variable volume.

14. The apparatus of claim 1, wherein the enclosure comprises flexible sides.

15. The apparatus of claim 1, wherein the enclosure comprises concertinaed sides.

16. The apparatus of claim 1, wherein the enclosure is a bellows.

17. An apparatus for negative-pressure treatment, the apparatus comprising:
   a dressing;
   an enclosure having a variable volume and a port;
   a container fluidly coupled to the dressing through the enclosure;
   a first one-way valve coupled to the port and configured to allow fluid ingress to the enclosure from the dressing through the port;
   a second one-way valve coupled to the port and configured to allow fluid egress from the enclosure to the container through the port; and
   an actuator comprising a shaft and contact surface, the shaft and contact surface configured to be driven linearly to apply a linear force to the enclosure;
   wherein the variable volume is configured expand to generate a negative pressure in a range of about 115 mmHg to about 135 mmHg in response to the linear force being removed from the enclosure.

18. The apparatus of claim 17, wherein the actuator configured to be decoupled from the enclosure.

19. The apparatus of claim 17, wherein the enclosure is configured to maintain a therapeutic negative pressure in the dressing.

20. The apparatus of claim 19, wherein the therapeutic negative pressure is in a range of about 115 mmHg to about 135 mmHg.

21. The apparatus of claim 17, wherein the actuator is an electro-mechanical actuator and is fluidly isolated from the variable volume.

22. The apparatus of claim 17, wherein the enclosure comprises flexible sides.

23. The apparatus of claim 17, wherein the enclosure comprises concertinaed sides.

24. The apparatus of claim 17, wherein the enclosure is a bellows.

25. A method of providing negative-pressure treatment to a tissue site, the method comprising:
    placing a tissue interface proximate to the tissue site;
    placing a cover over the tissue interface;
    sealing the cover to an attachment surface peripheral to the tissue site;
    fluidly coupling the tissue interface to an enclosure having a variable volume through a port;
    fluidly coupling a container to the tissue interface through the enclosure via the port;
    detachably coupling the enclosure to an actuator, the actuator comprising a shaft and contact surface;
    extending the shaft and contact surface of the actuator linearly to apply a linear force on the enclosure to compress the variable volume and expel fluid from the enclosure through the port; and
    retracting the shaft and contact surface of the actuator linearly to remove the linear force from the enclosure to allow the variable volume to expand and draw fluid from the tissue site into the enclosure via the port;
    wherein the expansion of the variable volume generates negative pressure in a range of about 115 mmHg to about 135 mmHg.

26. The method of claim 25, wherein the actuator is fluidly isolated from the variable volume.

27. The method of claim 25, wherein the enclosure comprises flexible sides.

28. The method of claim 25, wherein the enclosure is a bellows.

29. The method of claim 25, wherein compressing the variable volume expels fluid through a one-way valve to the container.

30. The method of claim 25, further comprising decoupling the enclosure from the actuator.

* * * * *